United States Patent [19]

Ramsner et al.

[11] Patent Number: 4,756,200
[45] Date of Patent: Jul. 12, 1988

[54] PROBE FOR EXTRACTING HOT SAMPLE GAS

[75] Inventors: Wolfgang Ramsner, Haidershofen; Karl Ruemer, Linz; Kurt Hölzl, Sarleinsbach, all of Austria

[73] Assignee: Voest-Alpine Aktiengesellschaft, Linz, Austria

[21] Appl. No.: 30,149

[22] Filed: Mar. 25, 1987

[30] Foreign Application Priority Data

Apr. 29, 1986 [EP] European Pat. Off. ........ 86890120.8

[51] Int. Cl.$^4$ ............................................. G01N 1/22
[52] U.S. Cl. .............................. 73/863.11; 73/864.73
[58] Field of Search ........... 73/863.11, 863.12, 864.73, 73/864.74

[56] References Cited

U.S. PATENT DOCUMENTS 4,594,904  6/1986  Richter ................. 73/863.11 X

FOREIGN PATENT DOCUMENTS 3305232  8/1984  Fed. Rep. of Germany .
2133081  11/1972  France .
85/00179  1/1985  PCT Int'l Appl. .

Primary Examiner—Tom Noland
Attorney, Agent, or Firm—Kurt Kelman

[57] ABSTRACT

A probe for extracting a hot gas sample comprises an inner tube for conducting the hot gas sample and a cooling jacket surrounding the inner tube. A heating element surrounds the inner tube and the heated inner tube is shielded from the cooling jacket by an interposed heat insulation.

1 Claim, 1 Drawing Sheet

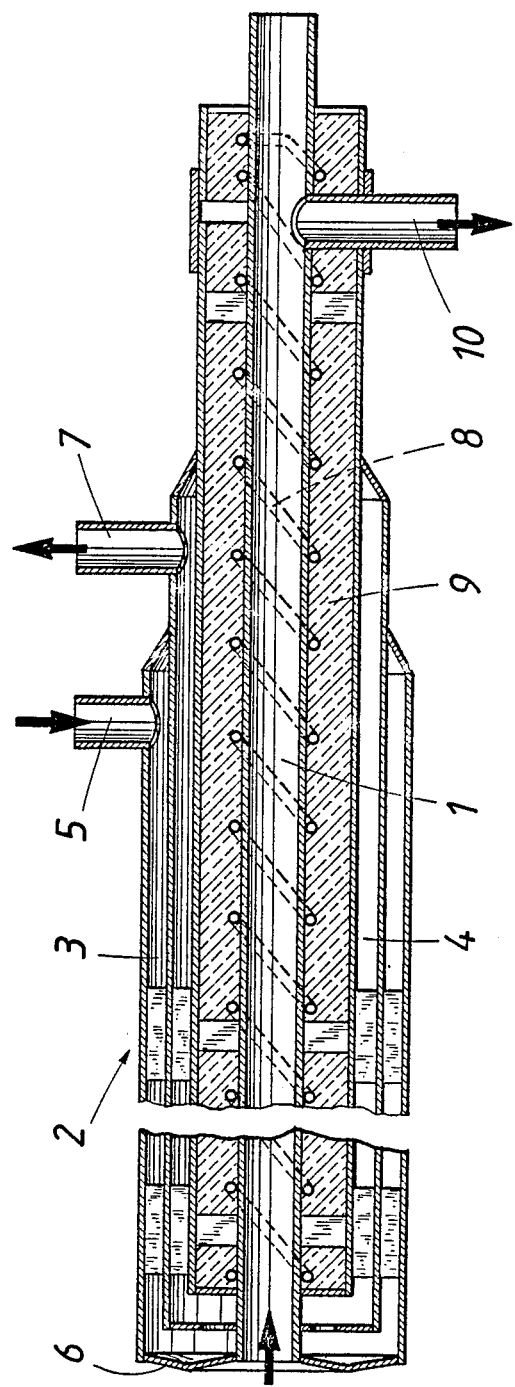

PROBE FOR EXTRACTING HOT SAMPLE GAS

BACKGROUND OF THE INVENTION

1. Field of the Invention

This invention relates to a probe for extracting hot sample gas, which probe comprises an inner tube for conducting sample gas and a jacket, which surrounds the inner tube and defines a passage for conducting a liquid coolant.

2. Description of the Prior Art

If processes in which hot gases are formed are to be controlled in dependence on the composition of said hot gases, sample gas must be extracted from the reaction chamber through an extraction probe. Being exposed to the high temperatures of the hot gases, the outside surfaces of the extraction probes must be cooled. On the other hand, the cooling of the outside surface of the probes may result in a temperature drop below the dew point temperature of the sample gas being extracted so that condensate may undesirably form in the inner tube of the extraction probe. A condensation will be particularly undesirable if the sample gas is dust-laden, such as is the case, e.g., during the calcination of a ground mixture of the raw materials used in the production of cement. Dust entrained by the gas will mix with the condensate to form a sludge, which may form a crust on the inner tube of the extraction probe and may restrict the flow area therein. It is known that such a temperature drop below the dew point temperature can be avoided in that at least in the inner tube for conducting the sample gas the coolant is always maintained at a temperature above the dew point temperature of the sample gas. But such cooling will require a relatively expensive control and will give rise to special problems in all cases in which the dew point temperature of the sample gas exceeds the evaporation temperature of the liquid coolant consisting in most cases of water.

SUMMARY OF THE INVENTION

It is an object of the invention to improve an extraction probe of the kind described first hereinbefore so that a formation of condensate in the inner tube of the cooled extraction probe can reliably be precluded.

It is another object of the invention to provide such an extracting probe in which the evaporation of a liquid coolant used in the probe will be prevented even when the dew point temperature of the sample gas exceeds the evaporation temperature of the liquid coolant.

This object is accomplished in accordance with the invention in that the inner tube is provided with heating means and is shielded by heat insulation from the cooled outside surface of the probe.

Because heat insulation is provided between the inner tube and the cooled outside surface of the extracting probe an influence of the temperature of the liquid coolant on the temperature of the wall of the inner tube can be prevented in a simple manner so that the inner tube can be maintained at a desired temperature by heating means regardless of the temperature of the cooled outside surface of the probe. In this manner a temperature drop below the dew point temperature of the sample gas in the inner tube can reliably be avoided even in the unfavorable cases in which the dew point temperature of the sample gas being extracted exceeds the evaporation temperature of the liquid coolant conducted in the jacket of the probe. As a result, expensive control means for the cooling circuit are not required because it is sufficient to ensure that the temperature of the liquid coolant will be maintained below its evaporation temperature.

The inner tube of the extraction probe may be heated by any suitable means which are adapted to sufficiently heat the inner tube. Particularly desirable conditions will be obtained if the inner tube of the extraction probe is heated by an electric resistance heater because such electric resistance heater can be controlled in a simple manner in dependence on the temperature of the inner tube.

BRIEF DESCRIPTION OF THE DRAWING

The drawing is a simplified axial sectional view showing an embodiment of a probe according to the invention for extracting hot sample gas.

DETAILED DESCRIPTION OF THE PREFERRED EMBODIMENT

An embodiment of the invention will now be described more in detail with reference to the drawing.

The probe for extracting hot sample gas comprises an inner tube 1 for conducting sample gas and a jacket 2, which surrounds the inner tube and is formed with two concentric annular spaces 3 and 4 for conducting a liquid coolant. The liquid coolant is supplied to the outer annular space 3 through a port 5 and is conducted in said outer annular space 3 of the jacket 2 toward that end 6 of the extraction probe at which the sample gas enters said probe. Near that end 6 of the probe the liquid coolant is reversed to flow in the inner annular space 4 to a port 7, which is connected to a return line for the liquid coolant. Owing to the cooling effected by the liquid coolant, that end 6 of the extraction probe which serves to receive the sample gas and is exposed to the hot gases in the reaction chamber will not be excessively heated.

To prevent in spite of such cooling of the jacket 2 of the probe a temperature drop in the inner tube 1 below the dew point temperature of the sample gas being extracted, the inner tube 1 is heated by heating means 8 consisting of at least one electric resistance heater that is helically wound around the inner tube. By said heating means the inner tube is heated to a temperature above the dew point temperature of the sample gas being extracted through the inner tube. A mutual influence of the coolant in the jacket 2 and the heating means 8 for the inner tube 1 of the extracting probe is prevented by the provision of suitable heat insulation 9 between the inner tube and the jacket 2. As a result, the sample gas flowing through the inner tube 1 can be withdrawn through a gas port 10 without a formation of condensate within the extracting probe and can be supplied, e.g., to a filter. The heating means 8 may be controlled by a thermostat, which is connected to the inner tube 1 adjacent to the gas port 10 and energizes the heating means 8 as soon as the temperature of the inner tube adjacent to its relatively cold outlet and exceeds a predetermined temperature limit.

We claim:

1. A probe for extracting a hot sample gas, which comprises
   an inner tube for conducting the hot sample gas,
   a jacket surrounding the inner tube and adapted to conduct a liquid coolant, and
   the improvement comprising
   heating means for the inner tube and
   heat insulation means disposed between said inner tube and said jacket, the heating means being disposed between the jacket and the heat insulation means.

* * * * *